(12) United States Patent
Wernet et al.

(10) Patent No.: US 9,395,226 B2
(45) Date of Patent: Jul. 19, 2016

(54) APPARATUS FOR DETERMINING AND/OR MONITORING A PROCESS VARIABLE

(75) Inventors: Armin Wernet, Rheinfelden (DE); Roland Dieterle, Lorrach (DE)

(73) Assignee: ENDRESS + HAUSER GMBH + CO. KG, Maulburg (DE)

( * ) Notice: Subject to any disclaimer, the term of this patent is extended or adjusted under 35 U.S.C. 154(b) by 232 days.

(21) Appl. No.: 12/448,355

(22) PCT Filed: Nov. 30, 2007

(86) PCT No.: PCT/EP2007/063074
§ 371 (c)(1),
(2), (4) Date: Jan. 12, 2010

(87) PCT Pub. No.: WO2008/074611
PCT Pub. Date: Jun. 26, 2008

(65) Prior Publication Data
US 2010/0141285 A1    Jun. 10, 2010

(30) Foreign Application Priority Data
Dec. 20, 2006   (DE) .......................... 10 2006 060 921

(51) Int. Cl.
*G01R 31/20* (2006.01)
*G01F 23/24* (2006.01)
*G01F 23/26* (2006.01)
*C12Q 1/00* (2006.01)

(52) U.S. Cl.
CPC ................ *G01F 23/24* (2013.01); *G01F 23/26* (2013.01); *C12Q 1/00* (2013.01); *C12Q 2304/00* (2013.01); *G01N 2201/00* (2013.01)

(58) Field of Classification Search
CPC ........ C12Q 1/00; C12Q 2304/00; B82Y 5/00; G01K 1/00; G01K 2201/00; G01N 1/00; G01N 2201/00
USPC ................ 324/126, 754.04, 754.24; 73/1.73, 73/304 C
See application file for complete search history.

(56) References Cited

U.S. PATENT DOCUMENTS

| | | | | |
|---|---|---|---|---|
| 2,534,899 A | * | 12/1950 | Casanova ...................... | 315/121 |
| 2,607,220 A | * | 8/1952 | Martin .................... | E21B 47/06 |
| | | | | 340/855.3 |
| 3,879,644 A | | 4/1975 | Maltby | |
| 4,284,951 A | * | 8/1981 | Dahl et al. ..................... | 324/430 |
| 4,435,681 A | * | 3/1984 | Masuda et al. ................ | 324/459 |
| 4,465,088 A | * | 8/1984 | Vosper ............................. | 137/1 |
| 4,468,611 A | * | 8/1984 | Tward .................. | G01N 27/226 |
| | | | | 324/673 |
| 4,499,767 A | * | 2/1985 | Fathauer et al. ............ | 73/304 C |
| 4,535,637 A | * | 8/1985 | Feller .......................... | 73/861.77 |
| 4,888,989 A | | 12/1989 | Homer | |
| 4,985,682 A | * | 1/1991 | Boryta .......................... | 324/557 |
| 5,546,006 A | * | 8/1996 | Louge ........................... | 324/688 |

(Continued)

FOREIGN PATENT DOCUMENTS

WO    WO 96/29580    9/1996

*Primary Examiner* — Joshua Benitez-Rosario
*Assistant Examiner* — Temilade Rhodes-Vivour
(74) *Attorney, Agent, or Firm* — Bacon & Thomas, PLLC

(57) ABSTRACT

An apparatus for determining and/or monitoring at least one process variable of a medium. The apparatus includes at least one probe unit and at least one electronics unit, which supplies the probe unit with an electrical, exciter signal and which receives from the probe unit an electrical, measurement signal. The invention includes, that the probe unit has at least one inner electrode and at least one outer electrode surrounding the inner electrode.

10 Claims, 2 Drawing Sheets

(56) References Cited

U.S. PATENT DOCUMENTS

| | | | | |
|---|---|---|---|---|
| 5,604,441 | A * | 2/1997 | Freese, V | G01N 27/221 |
| | | | | 324/663 |
| 5,858,199 | A * | 1/1999 | Hanak | 205/687 |
| 5,885,434 | A * | 3/1999 | Suda et al. | 205/81 |
| 5,989,477 | A * | 11/1999 | Berger | 264/446 |
| 5,992,251 | A * | 11/1999 | Grieger et al. | 73/866.5 |
| 6,342,187 | B1 * | 1/2002 | Jacob et al. | 422/186.05 |
| 6,370,426 | B1 * | 4/2002 | Campbell et al. | 600/547 |
| 6,512,358 | B2 * | 1/2003 | Klofer et al. | 324/103 P |
| 6,551,558 | B1 | 4/2003 | Mann | |
| 7,880,479 | B2 * | 2/2011 | Liao et al. | 324/679 |
| 7,924,027 | B2 * | 4/2011 | Sieckmann et al. | 324/662 |
| 8,217,661 | B2 * | 7/2012 | Wernet et al. | 324/537 |
| 8,354,850 | B2 * | 1/2013 | Soerensen et al. | 324/658 |
| 8,400,141 | B2 * | 3/2013 | Wernet et al. | 324/126 |
| 8,432,171 | B2 * | 4/2013 | Coppe et al. | 324/663 |
| 2005/0194250 | A1 * | 9/2005 | Frey | C12Q 1/6837 |
| | | | | 204/403.01 |
| 2006/0219002 | A1 * | 10/2006 | Florenz | 73/304 C |
| 2007/0101811 | A1 * | 5/2007 | Nyce | G01F 23/68 |
| | | | | 73/304 C |
| 2010/0005880 | A1 * | 1/2010 | Dieterle et al. | 73/304 R |
| 2010/0109649 | A1 * | 5/2010 | Dieterle et al. | 324/126 |
| 2010/0141285 | A1 * | 6/2010 | Wernet | G01F 23/26 |
| | | | | 324/754.22 |
| 2010/0154534 | A1 * | 6/2010 | Hampton | 73/304 C |
| 2010/0194383 | A1 * | 8/2010 | Dieterle et al. | 324/149 |

\* cited by examiner

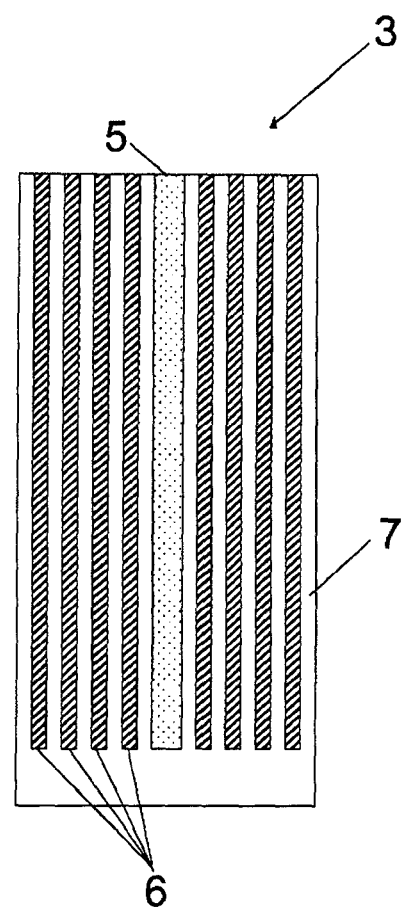

APPARATUS FOR DETERMINING AND/OR MONITORING A PROCESS VARIABLE

TECHNICAL FIELD

The invention relates to an apparatus for determining and/or monitoring at least one process variable of a medium. The apparatus includes: at least one probe unit; and at least one electronics unit, which supplies the probe unit with an electrical, exciter signal and which receives from the probe unit an electrical, measurement signal. The medium is, for example, a liquid, a bulk good or a fluid. The process variable is, for example, the fill level of the medium.

BACKGROUND DISCUSSION

In process and automation technology, it is known to determine or monitor the fill level of a medium by means of the capacitive measuring method. In this method, a probe and the wall of the container, or a second probe unit, form, with the medium as dielectric, a capacitor. The capacitance of this capacitor is measured and, based on its value, the fill level is ascertained. A problem with this method is that the probe unit comes into contact with the medium and that, consequently, accretion formation can occur on the probe unit. Such accretion degrades the measuring, or, in general, prevents measurement. In the state of the art, it is known to supply the probe unit with a relatively high measuring frequency (e.g. greater than 1 MHz), in order to improve insensitivity to accretion. Disadvantageous with a high measuring frequency is that this is accompanied by a reduction of the allowable, maximum probe length. This is brought about by frequency dependent resonance effects arising on the probe, which prevent a linear measuring. It is necessary, thus, to find a compromise between a large probe length (e.g. greater than 10 m) and a good insensitivity to accretion.

SUMMARY OF THE INVENTION

An object of the invention is to provide a measuring device, in the case of which, at a predetermined probe length, a maximum accretion insensitivity can be set.

The object is achieved according to the invention by features including that the probe unit has at least one inner electrode and at least one outer electrode surrounding the inner electrode. The invention resides, thus, in the fact that at least one outer electrode is arranged around the inner electrode. In an embodiment, there are at least two outer electrodes. The inner electrode and the outer electrode, or the outer electrodes, are, in an embodiment, electrically unconnected. In an embodiment, the inner electrode or at least one of the outer electrodes is supplied with the exciter signal. The measurement signal is then tapped from the electrode supplied with the exciter signal.

In an embodiment, at least two outer electrodes are provided, which differ from one another essentially in their distances to the inner electrode, which they surround. Correspondingly, the electrodes differ from one another by their distances from the outer surface of the probe unit, i.e. the outer electrodes have, thus, in each case, a different distance to the medium.

An embodiment includes, that the inner electrode and the outer electrode are insulated electrically relative to one another and relative to the medium. The electrodes are, in each case, isolated by insulation relative to one another and relative to the medium.

An embodiment provides, that the inner electrode is embodied to be rod shaped or cable shaped.

An embodiment includes, that the outer electrode is embodied, at least sectionally, to be tubular.

An embodiment provides, that the probe unit has at least two outer electrodes, and that the outer electrodes have equal wall thickness.

An embodiment includes, that the outer electrode is embodied in such a manner, that the outer electrode coaxially surrounds the inner electrode. In an embodiment, thus, the rod-shaped inner electrode is concentrically surrounded by at least one outer electrode, or by a plurality of outer electrodes.

An embodiment provides, that the electronics unit is embodied in such a manner, that the electronics unit supplies the inner electrode and/or the outer electrode with the exciter signal. In an embodiment, in which at least two outer electrodes are provided, the electronics unit is embodied in such a manner, that the electronics unit supplies the inner electrode and/or at least one of the outer electrodes with the exciter signal.

An embodiment includes, that the electronics unit is embodied in such a manner, that the electronics unit supplies the inner electrode and/or the outer electrode in a predeterminable sequence with the exciter signal. The outer electrodes are, thus, in an embodiment, supplied with the exciter signal at different points in time.

An embodiment provides, that at least two outer electrodes are provided, and that the electronics unit is embodied in such a manner, that the electronics unit supplies the inner electrode and the outer electrodes alternately with the exciter signal. In an embodiment, this alternating supplying is performed at the installation of the measuring device, while, in the case of another embodiment, it is on a rotating schedule, and, in the case of an additional embodiment, on the basis of a manual triggering. Especially, the measurement signal is tapped from that electrode, which is supplied with the exciter signal. The probe unit of the invention is, thus, provided with a number of electrodes, which all can be supplied with the exciter signal and from which the measurement signal is receivable. The electrodes are, in such case, embodied and arranged in such a manner, that the distance between electrode and medium is, in each case, different, i.e. the insulation between electrode and medium has, in each case, a different thickness.

An embodiment includes, that the electronics unit is embodied in such a manner, that the electronics unit receives and evaluates the measurement signals associated with the individual supplyings of the inner electrode and the outer electrodes with the exciter signal. Since the individual electrodes are supplied, a curve of measurement signal as a function of the different excitings can be determined and differences compared with expected values. By the course of the offset between the individual excitings of the individual electrodes, as ascertained during scan through, it can be ascertained, with which electrode the best measurement result can be obtained. A criterion therefor is: from when do the offset differences, to a predetermined approximation, lie about on a line, whose slope is determined by the design of the probe unit and is, thus, known? For understanding, this can also be explained as follows: If one scans through all electrodes during the empty calibration (i.e. the medium is not contacting the probe unit) and during the full calibration (i.e. the probe unit is completely covered by the medium), then, in the case of a certain fill level (e.g. 50%), the fill levels calculated from the capacitances for each electrode must lie on a line with slope 0. If this is not the case, then the cause therefor is an accretion on the probe unit, when the deviation is in the case of the inner electrode, or resonance effects form the cause, when the deviation occurs in the case of measuring with the outer electrodes. In an embodiment, consequently, used for the measurements is that electrode, with whose capacitance the minimal fill level can be calculated, wherein the deviations usually have a positive sign. With the probe unit of the invention, thus, also in the case of supplying the individual electrodes and the evaluation of the measurement signals, for example, an accretion can be detected.

An embodiment provides, that the exciter signal is an alternating voltage.

An embodiment includes, that the electronics unit is embodied in such a manner, that the electronics unit produces the exciter signal in each case with the same frequency or with different frequencies.

In an embodiment, the exciter signal is placed on the inner electrode (rod) or on an outer electrode (pipe), and the other electrode, or in the case, that there are more than two outer electrodes, the other electrodes, is/are, in each case, allowed to float, i.e. it/they is/are connected with no electrical potential. Depending on operation of the electrodes, thus, different insulation thicknesses result between electrode and medium. In such case, accretion insensitivity improves with declining insulation thickness. Simultaneously, the opportunity for linear measuring with long probe units decreases. Therefore, it is possible to switch, depending on application, which electrode is supplied with the exciter signal for measuring. In an embodiment, this depends on the length of the probe. In an additional embodiment, the thicknesses of the insulation layers are different between inner electrode and outer electrodes, or between the individual outer electrodes. In an embodiment, the exciter signal in each measuring is applied sequentially to the individual electrodes (on the inner or one of the outers) and the respective measurement signals are registered separately from one another. In this way, quasi, from measuring to measuring, the insulation thickness between the supplied and, thus, for the measuring, active electrode and the medium is reduced. Between each measuring, from electrode to electrode, there is usually a known offset, which depends on geometry. If the offset changes between the individual measurements in the case of constant layer thicknesses, then one can deduce therewith the presence of accretion. Through a pass through of the measuring at the individual outer electrodes, furthermore, in an adjusting phase, it can be ascertained, which is the optimum insulation thickness for the present application (length of the probe) and then measuring is conducted correspondingly.

BRIEF DESCRIPTION OF THE DRAWINGS

The invention will now be explained in greater detail on the basis of the appended drawing, the figures of which show as follows:

FIG. 2 a section through a probe unit of the invention.

DETAILED DISCUSSION IN CONJUNCTION WITH THE DRAWINGS

Figure 1:
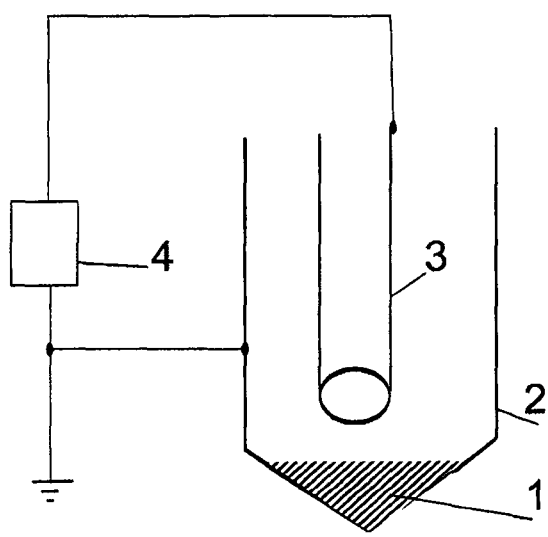
FIG. 1 a schematic drawing of an application of a measuring device of the invention.

FIG. 1 shows, in principle, the measuring method with the measuring device of the invention for measuring the process variable, fill level. The medium 1, which is, for example, a liquid or a bulk good, is located in the container 2. Also located in the container is the probe unit 3, which is connected electrically with the electronics unit 4. The probe unit 3 is supplied by the electronics unit 4 with the exciter signal, which is an electrical, alternating voltage signal. The probe unit 3 and the wall of the container 2 form with the medium 1 as dielectric a capacitor. This is for the case, in which the container 2 is an electrically conductive container. In an alternative embodiment (not shown), a second probe unit is provided as second electrode. From the measurement signal tapped from the probe unit 3, the capacitance of this capacitor can be ascertained. Its capacitance is, in such case, dependent on the fill level of the medium 1 as dielectric.

The measurement signal is, first, an electrical current signal, which, in most cases, is converted by a resistor into a voltage signal.

Depending on the character and conductivity of the medium 1, a jacketing unit is provided, which, on occasion, is composed, at least partially, of Teflon polytetrafluoroethylene. This serves to protect the probe unit 3 from the medium 1, or prevents an electrical short circuit between the probe unit 3 and the wall of the container 2, or the second electrode (not shown). In this case of the jacketing unit, the medium is not the dielectric of the measuring capacitor but, instead, the insulation is. The fill level is ascertained via the capacitance of the part of the probe insulation tapped with the conductive medium. The jacketing unit is, thus, the insulation of the electrodes in the probe unit 3 relative to the medium 1.

FIG. 2 shows a section through an embodiment of a probe unit 3 of the invention. The probe unit 3 of the invention includes a rod-shaped, inner electrode 5 and four, tubular, outer electrodes 6. The inner electrode 5 is, in such case, surrounded coaxially by the four, outer electrodes 6. All electrodes 5, 6 are cast in a jacketing unit 7. This jacketing unit 7 is, in such case, electrically non-conductive, i.e. it acts between the inner electrode 5 and the outer electrodes 6 and between the outer electrodes 6 and the medium as an insulating layer. The outer electrodes 6 have, in the illustrated version, equal wall thicknesses. In additional embodiments, the individual wall thicknesses and the non-conductive sections between inner electrode 5 and the, from the inner electrode 5 outwards, first, outer electrode 6, or between the outer electrodes 6 among themselves, can differ. Depending on the embodiment of the electronics unit 4, or the program stored in the electronics unit 4, the inner electrode 5 and the outer electrodes 6 are supplied with different exciter signals in different sequences. The exciter signal is, in such case, an electrical, alternating voltage. Depending on embodiment, in such case, the frequency of the exciter signal, as sent to the probe unit 3, is constant, or it varies, e.g. in continuous or discrete steps, or it is a superpositioning of a plurality of frequencies.

The probe unit 3 of the invention enables, thus, through its construction, a change of the insulation thickness between the electrode active for the measuring and the medium.

The invention claimed is:

1. An apparatus for capacitive determining and/or monitoring at least one process variable of a medium in a container, comprising:

at least one probe unit; and at least one electronics unit, which supplies said at least one probe unit with an electrical, exciter signal and which receives from said at least one probe unit an electrical, measurement signal, wherein:

said probe unit has at least one inner electrode and at least one outer electrode surrounding the inner electrode;

said at least one inner electrode and said at least one outer electrode are insulated electrically relative to one another and relative to the medium;

said at least one electronics unit is embodied in such a manner that it supplies said at least one inner electrode and said at least one outer electrode alternately with the exciter signal, and that it receives and evaluates the measurement signals associated with the individual supplyings of said at least one inner electrode and at least one said outer electrode.

2. The apparatus as claimed in claim 1, wherein:
said at least one inner electrode is embodied to be rod shaped or cable shaped.

3. The apparatus as claimed in claim 1, wherein:
said at least one outer electrode is embodied, at least sectionally, to be tubular.

4. The apparatus as claimed in claim 1, wherein:
said at least one outer electrode has equal wall thickness.

5. The apparatus as claimed in claim 1, wherein:
said at least one outer electrode is embodied in such a manner, that they coaxially surround said at least one inner electrode.

6. The apparatus as claimed in claim 1,
wherein: said exciter signal is an alternating voltage.

7. The apparatus as claimed in claim 6, wherein:
said at least one electronics unit is embodied in such a manner, that it produces the exciter signal with the same frequency or different frequencies.

8. The apparatus as claimed in claim 1, wherein:
said at least one electronics unit is embodied in such a manner that it supplies said at least one inner electrode or said at least one outer electrode in a predeterminable sequence with the exciter signal; and
the measurement signal is tapped from the electrode supplied with the exciter signal.

9. The apparatus as claimed in claim 1, wherein:
said at least one inner electrode and said at least one outer electrode is are all supplied with said exciter signal and said measurement signal is receivable from all of said at least one inner electrode and said at least one outer electrode.

10. An apparatus for measuring at least one process variable of a medium in a container, comprising:
at least one probe unit; and
at least one electronics unit, which supplies said at least one probe unit with an exciter signal and which receives from said at least one probe unit a measurement signal, wherein:
said probe unit has at least one inner electrode and at least two outer electrodes surrounding the inner electrode, wherein said at least two outer electrodes are tubular;
said at least one inner electrode and said at least two outer electrodes are insulated electrically relative to the medium;
said at least one electronics unit is embodied in such a manner that it supplies said at least one inner electrode and said at least two outer electrodes alternately with the exciter signal; and
the measurement signal is tapped from the electrode supplied with the exciter signal.

* * * * *